US010112038B2

(12) United States Patent
Ferguson (10) Patent No.: US 10,112,038 B2
(45) Date of Patent: Oct. 30, 2018

(54) UMBRELLA CHECK VALVE WITH REDUCED HEMOLYSIS (71) Applicant: VERNAY LABORATORIES, INC., College Park, GA (US)

(72) Inventor: Robert Ferguson, Newnan, GA (US)

(73) Assignee: VERNAY LABORATORIES, INC., College Park, GA (US)

( * ) Notice: Subject to any disclaimer, the term of this patent is extended or adjusted under 35 U.S.C. 154(b) by 0 days.

(21) Appl. No.: 15/019,125

(22) Filed: Feb. 9, 2016

(65) Prior Publication Data

US 2016/0228689 A1    Aug. 11, 2016

Related U.S. Application Data (60) Provisional application No. 62/113,951, filed on Feb. 9, 2015.

(51) Int. Cl.
| F16K 15/14 | (2006.01) |
| F16K 27/02 | (2006.01) |
| A61J 1/20 | (2006.01) |
| A61J 15/00 | (2006.01) |
| A61M 39/24 | (2006.01) |

(52) U.S. Cl.
CPC ............ *A61M 39/24* (2013.01); *A61J 1/2062* (2015.05); *A61J 15/0092* (2013.01);
(Continued)

(58) Field of Classification Search
CPC . Y10T 137/784; Y10T 137/789; F16K 15/14; F16K 15/148; F16K 27/0209;
(Continued)

(56) References Cited

U.S. PATENT DOCUMENTS 3,134,394 A * 5/1964 Ohta ...................... F16K 15/06
137/220
4,084,606 A    4/1978 Mittleman
(Continued)

FOREIGN PATENT DOCUMENTS

DE           1119068 B  * 12/1961 ............. F16K 15/14

OTHER PUBLICATIONS

PCT, International Search Report and Written Opinion, International Application No. PCT/US2016/017078 (dated Apr. 7, 2016).

*Primary Examiner* — Reinaldo Sanchez-Medina
*Assistant Examiner* — Hailey K Do
(74) *Attorney, Agent, or Firm* — Thompson Hine LLP (57) ABSTRACT A check valve assembly having a reduced net impact upon hemolysis, where the valve assembly has an elongated valve body including an inlet port, an outlet port, and an internal channel communicating between the ports, with each port disposed about and generally aligned with a central longitudinal axis of the body. The inlet port includes an umbrella-type check valve, and the internal channel is defined by three annular wall portions: a first annular wall portion aligned generally perpendicularly to the longitudinal axis to form a valve seat, a second annular wall portion that is generally concave, and a third annular wall portion that is generally convex, with the first, second and third annular wall portions forming an adjoining and essentially continuously curved, contiguous interior surface which smoothly redirects fluid flow toward the central longitudinal axis of the body and the outlet port.

12 Claims, 6 Drawing Sheets (52) U.S. Cl.
CPC ........ *F16K 15/148* (2013.01); *F16K 27/0209* (2013.01); *A61M 2039/2446* (2013.01); *A61M 2039/2466* (2013.01); *F16K 15/14* (2013.01); *Y10T 137/784* (2015.04); *Y10T 137/789* (2015.04)

(58) Field of Classification Search
CPC .... A61J 1/2062; A61J 15/0092; A61M 39/24; A61M 2039/2466; A61M 2039/2446
See application file for complete search history.

(56) References Cited

U.S. PATENT DOCUMENTS

| | | | | |
|---|---|---|---|---|
| 4,360,326 | A * | 11/1982 | Buchholz | F04C 29/02 137/854 |
| 6,062,248 | A * | 5/2000 | Boelkins | F16K 15/148 137/118.02 |
| 6,889,707 | B2 * | 5/2005 | Nicolino | F16K 15/148 137/513.3 |
| 7,243,676 | B2 | 7/2007 | Bailey | |
| 7,438,090 | B2 * | 10/2008 | Steele | F16K 15/141 137/515.5 |
| 8,230,875 | B2 * | 7/2012 | Norman | F16K 15/063 137/315.33 |
| 8,337,446 | B2 * | 12/2012 | Pokorney | A61F 2/2412 604/9 |
| 2008/0142102 | A1 * | 6/2008 | Savard | F04B 43/067 137/854 |
| 2014/0061245 | A1 | 3/2014 | McNulty et al. | |

* cited by examiner

UMBRELLA CHECK VALVE WITH REDUCED HEMOLYSIS

CROSS-REFERENCE TO RELATED APPLICATIONS

This application claims the benefit of U.S. Provisional Application No. 62/113,951, filed Feb. 9, 2015, which is incorporated herein by reference in its entirety.

FIELD

The present disclosure is directed to fluid control valves and, more particularly, to self-sealing fluid check valves used in medical equipment such as gravity-fed intravenous infusion sets, infusion pump administration sets, and similar equipment for delivering fluids to the circulatory system of a patient.

BACKGROUND

Figure 1:
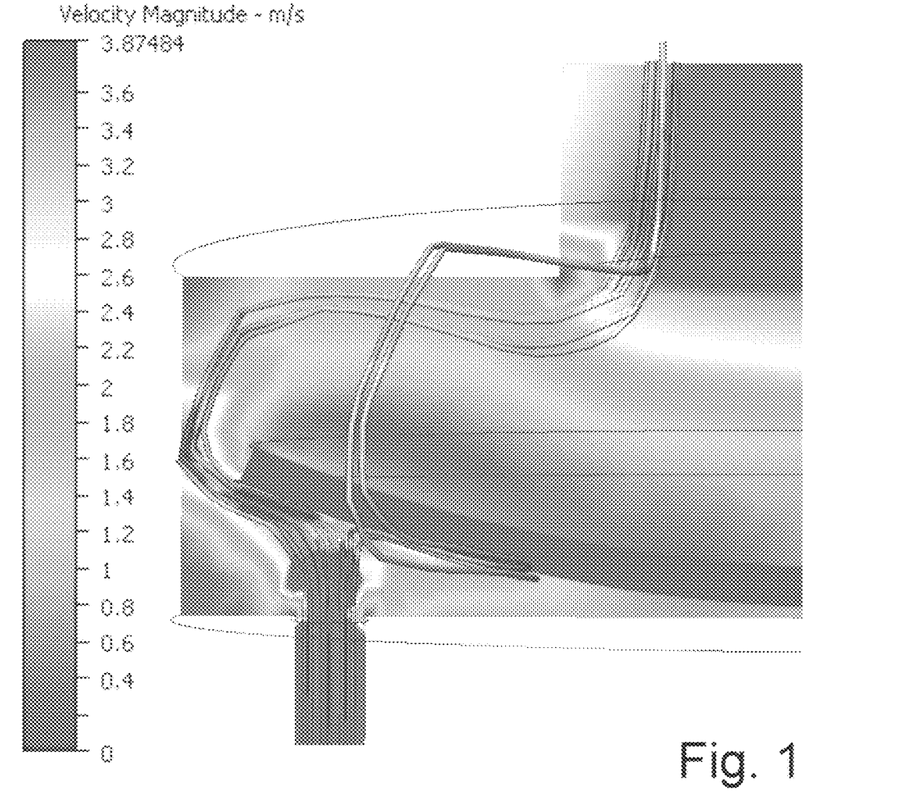
FIG. 1 is a side view of a simulated prior art, disk-type check valve illustrating a flow velocity field and exemplary flow paths for cells transiting an annular inlet port disposed adjacent to the periphery of the disk member. Such disk members are typically secured to the inlet-side of the valve body near or at the center of the disk (reflected but not specifically shown in this figure.)

Self-sealing fluid check valves are used in a variety of applications to control fluid flow through lines and devices, including in medical applications as components of gravity-fed and pump-driven intravenous infusion sets. Such check valves may be called "back check valves" or "non-return valves" or "one-way valves," and typically include a feature such as a duckbill valve, a ball valve, or most, commonly, a disc valve which engages with an adjacent valve seat in response to fluid flow in a selected direction. In an infusion line, a check valve is frequently used to prevent fluid backflow during IV therapy, e.g., after disconnection of a fluid supply such as a suspended infusion bag, or to prevent cross-flow during the parallel infusion of solutions through a single patient infusion line. Conventional check valves may be suitable for infusing saline, dextrose, or IV-delivered pharmaceutical solutions, but can cause significant levels of hemolysis, i.e. significant rupturing of erythrocytes or so-called red blood cells, when used during the infusion of packed cells or whole blood products into a patient. This is because the tortuous fluid path from the valve inlet, against the check valve, through the check valve or around the periphery of the check valve, and then across the lee side of the valve produces substantial fluid pressure changes, turbulence, and, most importantly, microscale shear forces that stress the cell membranes of erythrocytes entrained within the infusion fluid. An exemplary model of such a valve illustrating a flow velocity field and, indirectly, shear forces caused by flow velocity gradients is shown in FIG. 1 for reference.

SUMMARY

The applicant has developed an improved check valve assembly exhibiting reduced hemolysis when used to control the delivery of concentrated erythrocytes (packed red blood cells), whole blood products, and other cell-containing therapies. The check valve assembly is characterized by a umbrella-type check valve, positioned within the inlet port of a valve body, and surrounding wall portions that are essentially continuously curved to define an internal fluid channel that provides a less tortuous path for cells transiting around the check valve. The resultant smoothly curved flowpaths serve to reduce mechanical stresses caused by fluid pressure changes (as well as the potential for cavitation), acceleration and impact in turbulent flows, and, most importantly, dynamic shear stress caused by large velocity gradients within the valve assembly. In comparison to disc valves having essentially cylindrical walls and internal fluid channels, the check valve assembly reduces red blood cell loss during infusion therapy as well as the hemolytic activation of blood platelets and other associated complications.

In a first aspect, the check valve assembly has an elongated valve body including an inlet port, an outlet port, and an internal channel communicating between the ports, with each port disposed about and generally aligned with a central longitudinal axis of the body. The inlet port includes an umbrella-type check valve configured to obstruct reverse flow from the internal channel into the inlet port, and the internal channel is defined by three annular wall portions: a first annular wall portion aligned generally perpendicularly to the longitudinal axis to form a valve seat for the check valve; a second annular wall portion which is generally concave and adjoins the first annular wall portion, running from it toward the outlet port; and a third annular wall portion which is generally convex and adjoins the second annular wall portion, running from it toward the outlet port. The third annular wall portion may directly adjoin the outlet port or be separated from it by other curved or straight annular wall portions; however, at least the second and third annular wall portions form an essentially continuously curved interior surface that smoothly redirects fluid flow around the check valve toward the central longitudinal axis of the body.

In a second aspect, the check valve check assembly has an elongated valve body including an inlet port, an outlet port, and an internal channel communicating between the ports, with each port disposed about and generally aligned with a central longitudinal axis of the body. The inlet port includes an umbrella-type check valve configured to obstruct reverse flow from the internal channel into the inlet port, and an internal wall portion running from a valve seat toward the outlet port. The radial separation of the internal wall portion from the central longitudinal axis varies along the central longitudinal axis according to the functions:

$$r'=8+\mathrm{SQRT}(20.25-(x-4.5)^2) \text{ for } 0<x<4.5 \text{ and } r'>8; \quad \text{Equation (1)}$$

$$r'=0.0068{*}x^3-0.2242{*}x^2+1.5392{*}x+9.6571 \text{ for } 4.5<x<18.1; \quad \text{Equation (2)}$$

and $$r(x)=r'(x)\pm2.0, \quad \text{Equation (3)}$$

with the separation r defining an essentially continuously curved interior surface. Again, the internal wall portions and interior surface smoothly redirect fluid flow toward the central longitudinal axis of the body.

In a third aspect the check valve check assembly has an elongated valve body including an inlet port, an outlet port, and an internal channel communicating between the ports, with each port disposed about and generally aligned with a central longitudinal axis of the body. The inlet port includes an umbrella-type check valve configured to obstruct reverse flow from the internal channel into the inlet port, and an internal wall portion running from a valve seat toward the outlet port. The radial separation of the internal wall portion from the central longitudinal axis varies along the central longitudinal axis according to the functions:

$$r'=12.25+\mathrm{SQRT}(7.5625-(x-2.75)^2) \text{ for } 0<x<2.75 \text{ and } r'>12.25; \quad \text{Equation (4)}$$

$$r'=0.00003{*}x^5-0.002{*}x^4+0.0506{*}x^3-0.5724{*}x^2+ 2.1563{*}x+12.456 \text{ for } 2.75<x<18.1; \text{ and} \quad \text{Equation (5)}$$

$$r(x)=r'(x)\pm2.0, \quad \text{Equation (6)}$$

with the separation r defining an essentially continuously curved interior surface. Yet again, the internal wall portions and interior surface smoothly redirect fluid flow toward the central longitudinal axis of the body.

Those of skill will in the art appreciate that when the applicant states that "fluid flow is smoothly redirected around the check valve toward the central longitudinal axis of the body," this statement is made is with respect to an initial fluid flow from the inlet port and around the umbrella-type check valve, i.e., away from the central longitudinal axis of the body. Most fluid will not actually reach or cross the central longitudinal axis of the body before flowing through the outlet port of the valve body, but rather approach and then flow approximately parallel to that axis. An essentially continuously curved interior surface is one which lacks a significant discontinuity, such as a seam or ridge where the separation r increases or decreases as a step function by +/−0.25 units or more from adjoining portions of the surface.

DETAILED DESCRIPTION

As used herein, the term "a sealing portion" shall be interpreted to mean those portions of a check valve member that are proximate to a valve seat of the valve body. The "valve seat" shall be regarded as the surface or surfaces against which the sealing portion of the valve rests or abuts when the check valve member closes to prevent flow through the inlet port. It will be understood that at least the sealing portion must be displaced in order to alter the closure state of the check valve and check valve assembly.

Figure 2:
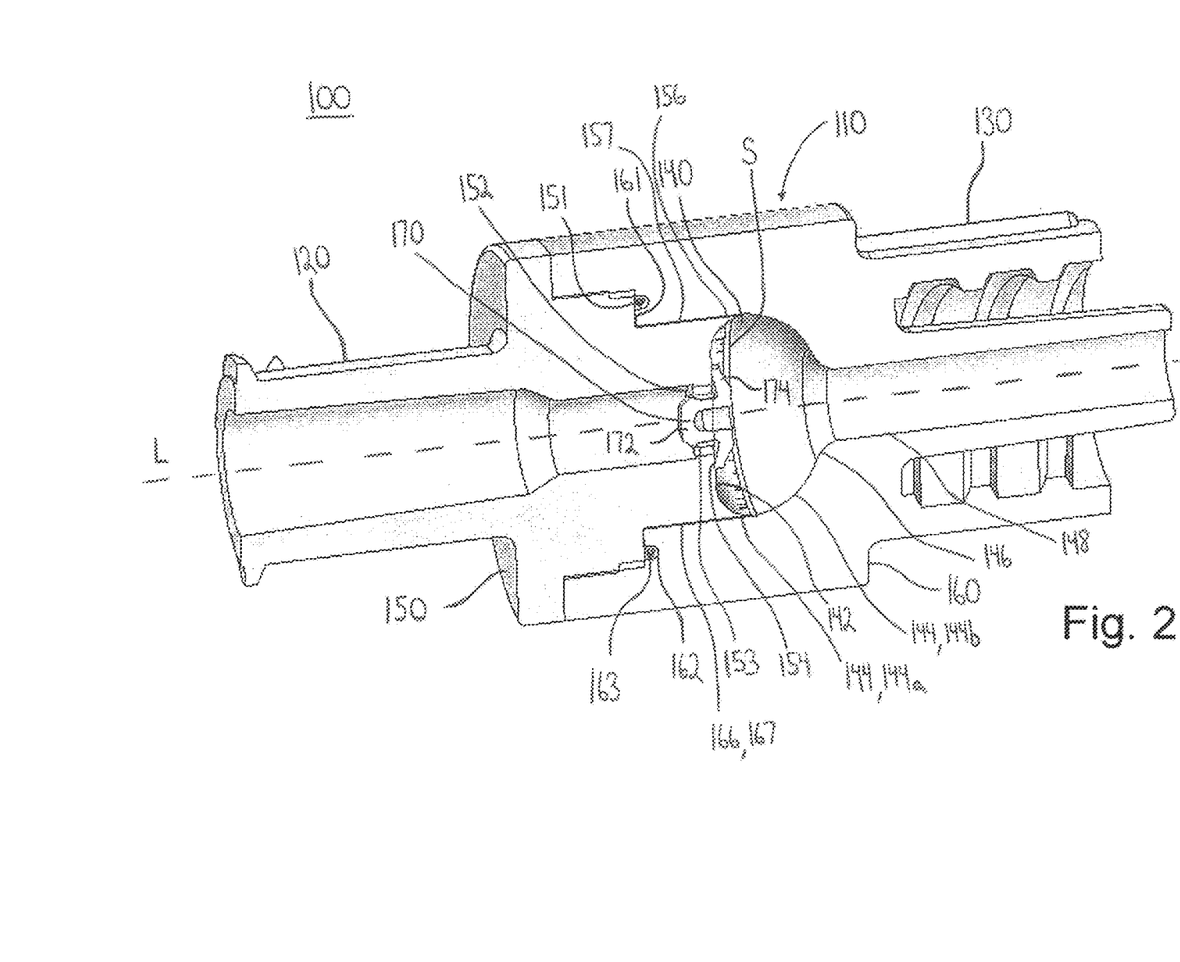
FIG. 2 is a cross-sectional view of a first embodiment.

In general, the present check valve assembly 100 includes an elongated valve body 110 having an inlet port 120, an outlet port 130, and an internal channel 140 fluidly communicating between the ports 120 and 130. As shown in FIG. 2, the inlet port 120 may provide a female luer fitting and the outlet port 130 may provide a male luer fitting, but those of skill will appreciate that the arrangement of the fittings may be reversed, that ports may both provide the same fitting, and that the ports may provide alternate fittings such as male and/or female threaded fittings, barbed fittings, compression fittings, or any other tubing-connector fitting adopted for medical use (for example, SMC and BPL series connectors marketed by Colder Products of St. Paul, Minn. and Nordson Corporation of Westlake, Ohio, respectively).

The elongated valve body 110 may be constructed from multiple parts, preferably from an inlet part 150 and an outlet part 160, which may be affixed to each other by, for example, ultrasonic welding, solvent welding, an epoxy, cyanoacrylate, or other medical grade adhesive, etc. The respective parts may then be permanently affixed to each other to provide a valve body 110 having a high burst strength in excess of 1000 psi. The valve body 110 can thus be manufactured using standard injection molding techniques while allowing for a curved internal channel 140 such as those described further below. In general, the inlet part 150 and outlet part 160 will mate about a line of separation "S" dividing the internal channel 140 at its widest point.

The inlet part 150 and outlet part 160 may include lands 151, 161 configured to abut against each other when the inlet part has been completely inserted within the outlet part, with at least one of the lands including an annular and longitudinally-facing groove, e.g., 162. In parts affixed to each other by solvent welding or adhesives, the groove may receive the solvent or adhesive so that these materials are less likely to be extruded into the internal channel 140 during assembly. The annular groove may receive a gasket 163 which becomes compressed between the lands 151, 161 so as to form a seal between the parts.

The check valve assembly 100 further includes an umbrella-type check valve 170 disposed over an inlet-side entrance to the internal channel 140. The umbrella-type check valve 170 conventionally includes a bulbous base 172 which engages with an inwardly-projecting flange 152 of the inlet part 150, as well as a diaphragm-shaped sealing disk 174 which selectively engages with an annular valve seat 154 disposed about the flange. The flange itself conventionally includes a plurality of apertures 153 which permit fluid to flow around the base 172, through the flange 152, and, upon displacing the sealing disk 174, past a valve seat 154 and sealing portion of the sealing disk 174 into the internal channel 140. However, in contrast to a disk valve, the umbrella valve 140 is self-centering within the inlet-side entrance, may be configured to have a very low cracking pressure (<2 kPa), and does not require gluing or an in-channel disk retention structure.

In general, a first annular wall portion 142 of the internal channel 140 is aligned perpendicularly to a central longitudinal axis "L" of the valve body and to define the initial portion of the interior surface of the channel (with respect to the expected direction and manner of fluid flow). This first annular wall portion defines the valve seat 154 against which the sealing portion of the sealing disk 174 engages during reverse flow. A second annular wall portion 144 of the internal channel 140 adjoins the first annular wall portion 142 and is concave with respect to the internal channel, i.e., curves toward the central longitudinal axis L of the body 110 with increasing distance along axis L. This second annular wall portion defines the next portion of the interior surface of the channel, and serves to smoothly redirect fluid flow toward the central longitudinal axis L. A third annular wall portion 146 of the internal channel 140 adjoins the second annular wall portion 144 and is convex with respect to the internal channel, i.e., curves away from the central longitudinal axis L of the body 110 with increasing distance along axis L. This third annular wall portion defines the following portion of the interior surface of the channel and also serves to smoothly redirect fluid flow toward the central longitudinal axis L, yet curves away from the central longitudinal axis so that fluid may ultimately flow parallel to that axis and out of the valve assembly 100. It will be appreciated that further annular wall portions, such as a straight annular wall portion 148, may be provided in order to form portions of a male fitting (as shown) or in order to better reestablish an essentially laminar flow regime within the confines of the valve assembly 100.

In the illustrated embodiments, the first annular wall portion 142 is aligned perpendicularly to the central longitudinal axis "L," although it is noted that in alternate embodiments the first annular wall portion may be aligned generally perpendicularly, deviating by +/−15 degrees from perpendicularity while still being considered to be "generally perpendicular." In addition, the first annular wall portion may itself be concave with respect to the internal channel 140. This is because the first annular wall portion both defines the valve seat 154 of the umbrella-type valve 170 and ideally runs parallel to the predominant direction of flow as fluid emerges from the valve. The valve assembly 110 may also be designed to have a very low cracking pressure (resistance to forward flow)—ideally 0.3 psi or less—and altering the geometry of the first annular wall portion 142 provides an additional way to alter the pre-load upon the sealing portion of the umbrella-type valve 142 in addition to changes in the thickness of the sealing disk 174 and the modulus of elasticity of the sealing disk material.

In an exemplary first embodiment, a second annular wall portion 144 may have a first subportion 144a which has a constant radius of curvature, and a second portion 144b which has a gradually increasing radius of curvature. This is because the second wall portion 144 must smoothly redirect outward flow from the umbrella-type valve 170 back inward toward the central longitudinal axis "L," but begin to recurve away from the central longitudinal axis to adjoin the convexly-curved third annular wall portion 146. For example, in a more specific second exemplary embodiment, the radial separation r' of the second annular wall portion 144 from the central longitudinal axis L may vary with distance x along the central longitudinal axis (where x=0 is the inlet-side entrance to the internal channel 140), in the first subportion 144a, according to:

$$r'=8+\text{SQRT}(20.25-(x-4.5)^2) \text{ for } 0<x<4.5 \text{ and } r'>8 \quad \text{Equation (1)}$$

where x, the constants 4.5, 8, and 20.25 (4.5^2), and r' are relative proportions, rather than distances with specific units of length. It will be appreciated that equation (1) is a guideline so that, while remaining a smooth function of x, the actual radial separation r may vary from r' by +/−2, and the actual longitudinal profile of the first portion may be semi-circular, semi-elliptical, or arcuate. Continuing the example, the radial separation r' may vary, in the second subportion 144b, according to:

$$r'=0.0068*x^3-0.2242*x^2+1.5392*x+9.6571 \text{ for } 4.5<x<10.99 \quad \text{Equation (2a)}$$

where each of x, the coefficients, the constants, and r' are relative proportions, rather than distances with specific units of length. Again, equation (2a) serves as a guideline so that, while remaining a smooth function of x, r may vary from r' by +/−2, and the actual longitudinal profile of the second portion may be described by differing coefficients and constants, a different order polynomial model, o a different mathematical model.

In the first exemplary embodiment, the third annular wall portion 146 has a gradually decreasing radius of curvature. This is because the this annular wall portion must smoothly funnel flow toward the exit of the internal channel 140 while avoiding sudden changes in curvature or surface continuity which might generate eddy currents, additional low pressure zones, or the like. For example, in the second embodiment the radial separation r' of the third annular wall portion 146 from the central longitudinal axis L may vary with distance x along the central longitudinal axis (where x=0 is the inlet-side entrance to the internal channel 140) according to the same relationship shown in equation (2a) but over a different portion of the longitudinal axis L:

$$r'=0.0068*x^3-0.2242*x^2+1.5392*x+9.6571 \text{ for } 10.99<x<18.1 \quad \text{Equation (2b)}$$

where, again, equation (2b) serves as a guideline so that, while remaining a smooth function of x, r may vary from r' by +/−2, and the actual longitudinal profile of the third annular wall portion may be described by differing coefficients and constants, a different polynomial, etc. Equations (2a) and (2b) collectively define Equation (2), as introduced earlier above.

Figure 3:
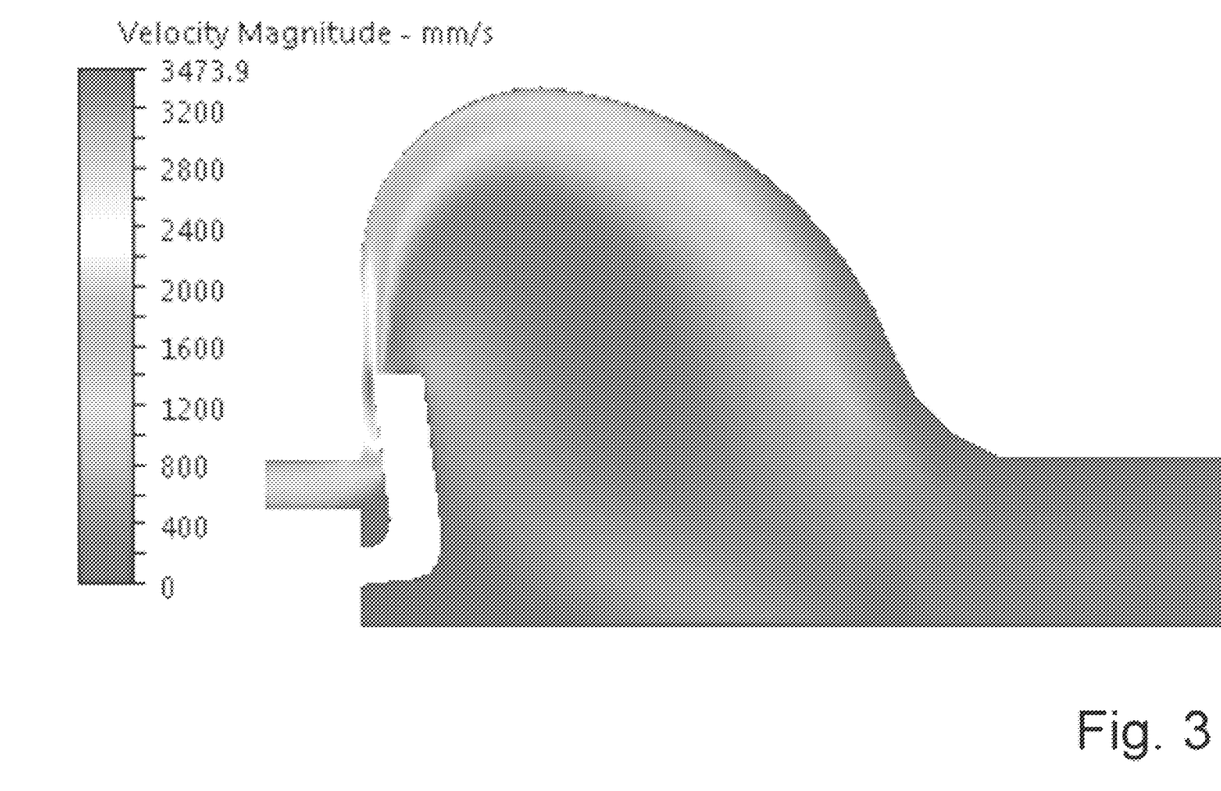
FIG. 3 is a is a side view of a simulated first embodiment illustrating a flow velocity field for cells transiting an umbrella-type check valve disposed within a central inlet port.

Finally, a fourth annular wall portion 148 may be provided in order to further separate the outlet-side exit of the internal channel 140 from the structure of the illustrated male luer fitting. This feature strengthens the base of the male projection and, as shown in FIG. 3, a fourth annular wall portion 148 would aid in ensuring a transition to laminar or laminar-like flow if the valve assembly 100 were to be used at higher flow rates. Thus the fourth annular wall portion 148 should be considered an optional feature of the embodiments.

FIG. 3 shows a simulated flow velocity field for fluid and cells passing through a valve assembly 100 of the exemplary first embodiment. The simulation is a two dimensional simulation of one half of the volume of the internal channel 140, but since most embodiments will be radially symmetric, the simulation is representative of the three dimensional flow field within such a device. Those of skill in the art will appreciate that, while not specifically illustrated, flow paths through the internal channel 140 will tend to follow the curvature of the wall portions 142, 144, 146, with some flow across the lee side of the umbrella-type valve 170. In contrast to FIG. 1, where flows paths impinge upon the walls of the interior space and include several abrupt changes in direction, FIG. 3 shows that there will be essentially one such region—where incoming fluid encounters and passes around the umbrella-type valve—in valve assemblies 100 like that of the first embodiment.

Figure 4:
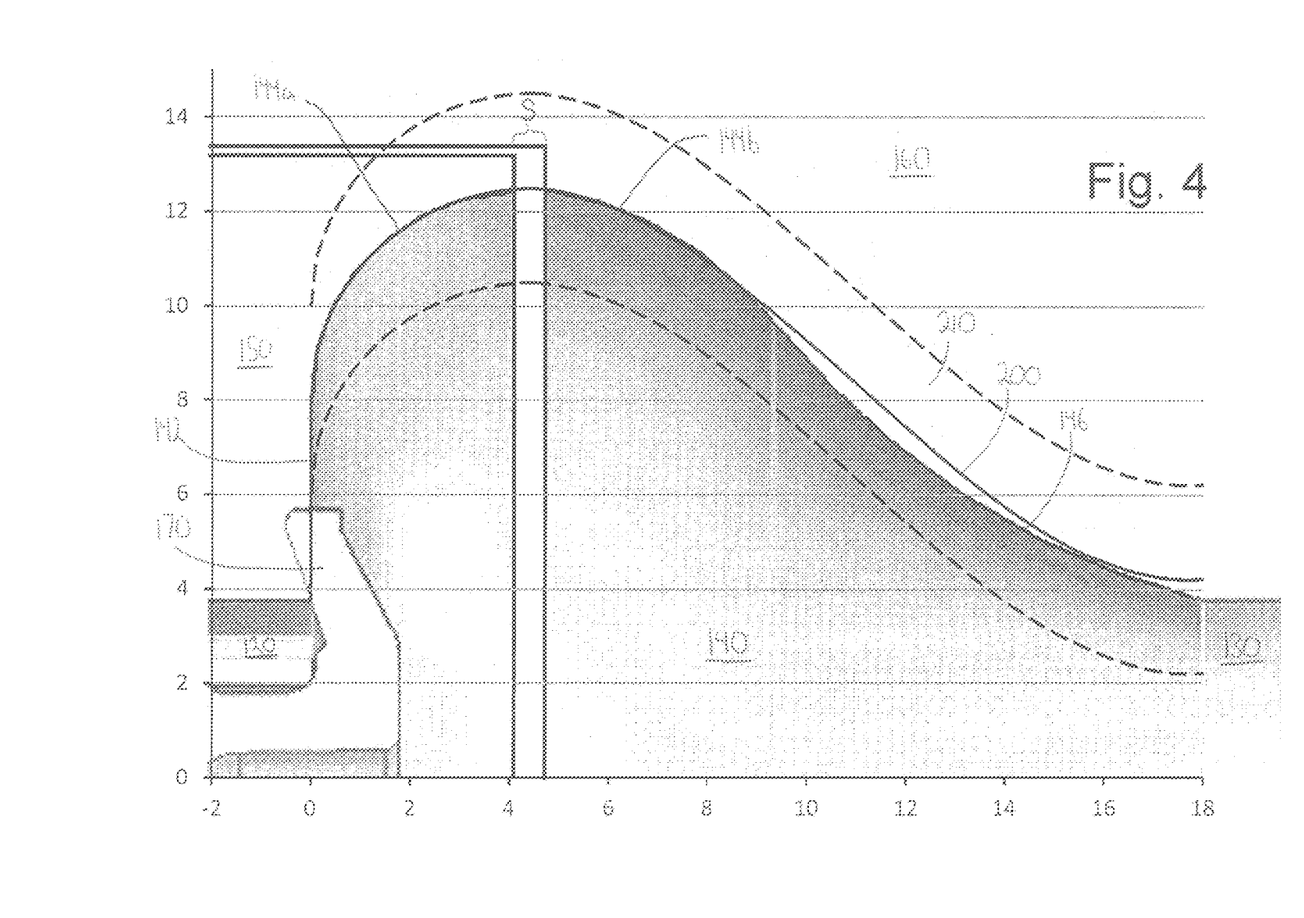
FIG. 4 is a partial cross-sectional view of a second embodiment detailing the relative proportions of first, second, and third annular wall portions with respect to a longitudinal axis (horizontal axis) and separation r from the longitudinal axis (vertical axis). A gap between first subportion 144a and second subportion 144b of the assembly is exaggerated for clarity of illustration.

FIG. 4 shows a cross-section of the exemplary second embodiment. The check valve assembly 100 includes a first annular wall portion 142 proximate the inlet port 120 and a second annular wall portion 144 having a both a first subportion 144a with a constant radius of curvature, following the r' of equation (1), and a second subportion 144b with an increasing radius of curvature, deviating from the r' of equation (2a) but remaining within the genus of wall portion curvatures permitted by equation (3). The reader will bear in mind that r(x) should remain a smooth function of x so as to produce an essentially continuously curved surface in order to minimize fluid pressure changes, turbulence, and microscale shear forces along the interior wall surface. It will be appreciated that in other embodiments the first sub portion 144a may be arcuately curved and deviate from the r' of equation (1), 200, within the range 210 permitted by equation (3) (illustrated by dashed lines bracketing line 200), just as the second annular wall portion 144 and second subportion 144b are shown to deviate from the r' of equation (2b), 200, within the range 210. The check valve assembly 100 of course includes that second subportion, as well as a third annular wall portion 146 with a decreasing radius of curvature, deviating from the r' of equation (2b) but in this instance converging back toward r' as the wall portion 146 approaches outlet port 130.

Figure 5:
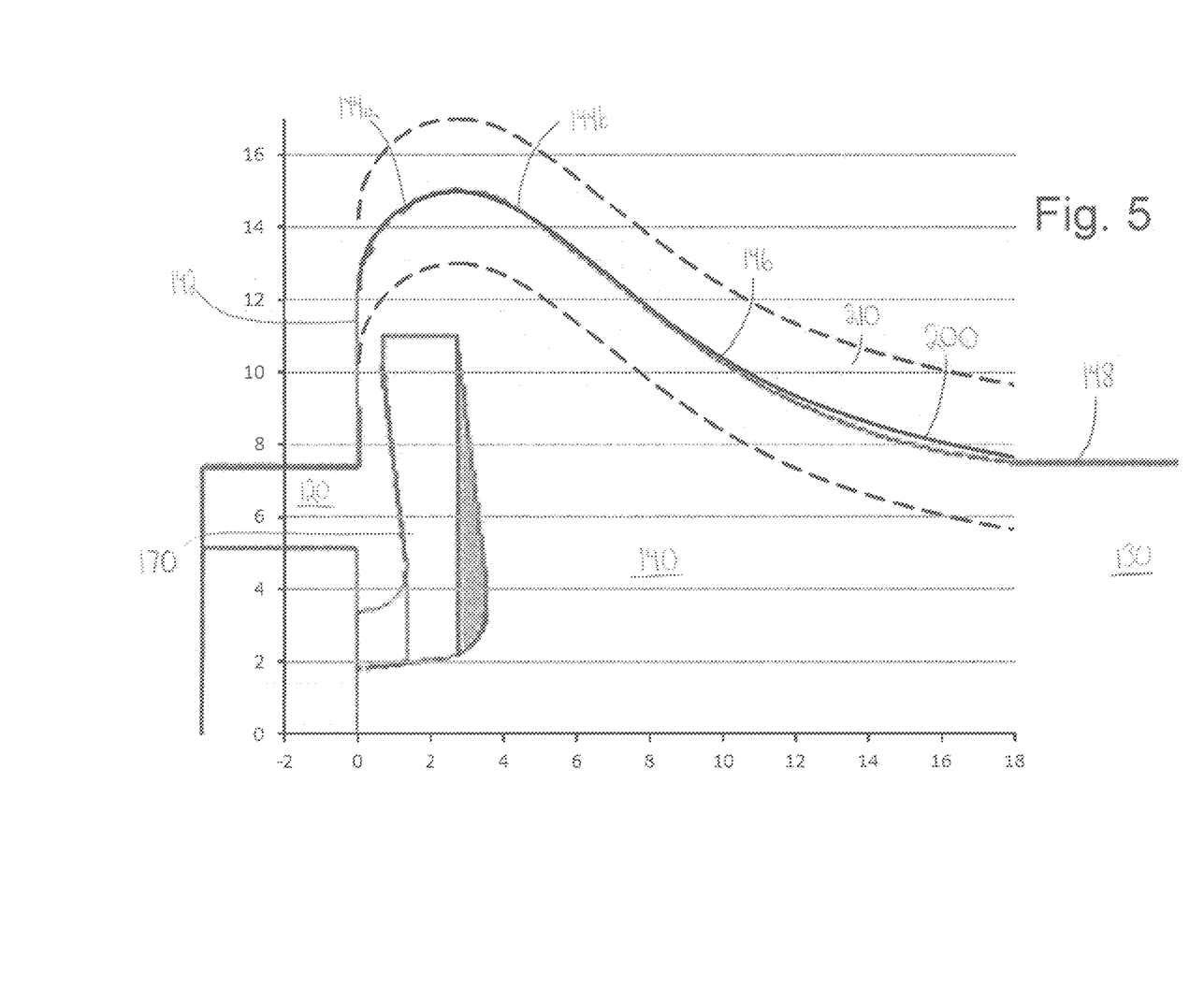
FIG. 5 is a partial cross-sectional view of a third embodiment detailing the relative proportions of first, second, and third annular wall portions with respect to a longitudinal axis (horizontal axis) and separation r from the longitudinal axis (vertical axis).

FIG. 5 shows a cross-section of an exemplary third embodiment. The check valve assembly 100 includes a first annular wall portion 142 proximate the inlet port 120 and an adjoining second annular wall portion 144 including a first subportion 144a where the radial separation r' from the central longitudinal axis L varies with distance x according to:

$$r'=12.25+\text{SQRT}(7.5625-(x-2.75)^2) \text{ for } 0<x<2.75 \text{ and } r'>12.25 \quad \text{Equation (4)}$$

with x, the constants, and r' representing relative proportions. The second annular wall portion 144 also includes a second subportion 144b where the radial separation r' from the central longitudinal axis L varies with distance x according to:

$$r'=0.00003*x^5-0.002*x^4+0.0506*x^3-0.5724*x^2+2.1563*x+12.456 \text{ for } 2.75<x<6.823 \quad \text{Equation 5(a)}$$

with x, the constants, the coefficients, and r' again representing relative proportions. The check valve assembly 100 also includes an adjoining third annular wall portion 146 where the radial separation r' from the central longitudinal axis L varies with distance x according to $$r'=0.00003*x^5-0.002*x^4+0.0506*x^3-0.5724*x^2+2.1563*x+12.456 \text{ for } 6.823<x<18.1 \quad \text{Equation 5(b)}$$

with x, the constants, the coefficients, and r' yet again representing relative proportions. Equations (5a) and (5b) collectively define Equation (5), as introduced earlier above.

Figure 6:
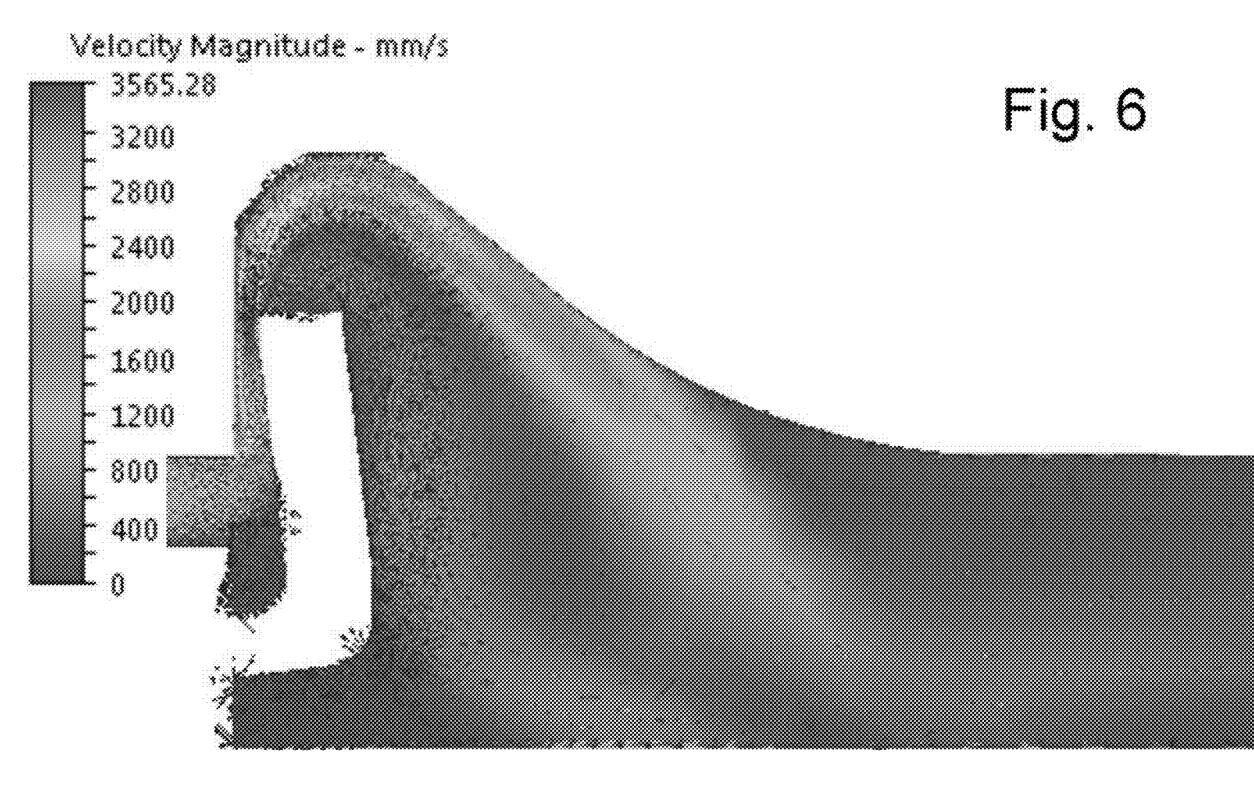
FIG. 6 is a side view of a simulated third embodiment illustrating a flow velocity field for cells transiting an umbrella-type check valve disposed within a central inlet port.

FIG. 6 shows a simulated flow velocity field for fluid and cells passing through a valve assembly 100 of the exemplary third embodiment. Again, in contrast to FIG. 1, where flows paths impinge upon the walls of the interior space and include several abrupt changes in direction, FIG. 6 shows that there will be essentially one such region—where incoming fluid encounters and passes around the umbrella-type valve—in valve assemblies 100 like that of the third embodiment.

As discussed earlier, the inlet part 150 and outlet part 160 mate about a line of separation "S" dividing the internal channel 140 at its widest point. In the illustrated embodiments, the line of separation falls between the first subportion 144a of the second annular wall portion 144 and the second subportion 144b of the portion 144, although there may be other embodiments where the second annular wall portion may be modeled or described via one or more other equations, or even provided with an arbitrary concave-curved profile, and thus not divided by a line of separation corresponding to anything other than a point of maximum width. To facilitate injection molding, at least part of the second annular wall portion 144, such as subportion 144a, may be molded as a longitudinally-projecting flange 156 (shown in FIGS. 2 and 4) extending from an cylindrical outer wall portion 157 of the inlet part 150. The outlet part 160 may then be provided with a socket 166 (shown in FIGS. 2 and 4) defined by a cylindrical inner wall portion 167 of the outlet part having a radius approximately equal to the separation of the second annular wall portion 144 from the central longitudinal axis L at the channel's widest point—i.e., equal to or slightly larger than the separation in order to accommodate practical limits upon the thinness of the projecting flange 156—to receive and engage the cylindrical outer wall portion 157. Those of skill will appreciate that the aforementioned "continuously curved inner surface" is described as an "essentially continuously curved inner surface" in part due to the presence of this line of separation and the likely presence of a de minimis inward- or outward-step in radial distance from the central longitudinal axis about that line due to practical limitations upon the dimensioning and tolerancing of the inlet and outlet parts 150, 160.

The various aspects and implementations described above are intended to be illustrative in nature, and are not intended to limit the scope of the invention. Any limitations to the invention will appear in the claims as allowed.

What is claimed is:

1. A check valve assembly comprising:
    an elongated valve body having an inlet port, an outlet port, and an internal channel communicating between said inlet port and said outlet port, each disposed about and generally aligned with a central longitudinal axis of the valve body;
    said inlet port including an umbrella check valve disposed at an entrance to said internal channel and configured to obstruct reverse flow from said internal channel into said inlet port;
    a distance along said central longitudinal axis from the entrance to said internal channel toward the outlet port being denoted as x, and the a radial separation of an interior wall of the internal channel from the central longitudinal axis being denoted as r, with r varying with x according to:

$$r'=8+\text{SQRT}(20.25-(x-4.5)^2) \text{ for } 0<x<4.5 \text{ and } r'>8; \quad \text{Equation (1)}$$

$$r'=0.0068*x^3-0.2242*x^2+1.5392*x+9.6571 \text{ for } 4.5<x<18.1; \quad \text{Equation (2)}$$

and $$r(x)=r'(x)\pm 2.0, \text{ where } \pm \text{ denotes a tolerance,} \quad \text{Equation (3)}$$

with the separation r defining an essentially continuously curved interior surface.

2. The check valve assembly of claim 1, wherein the elongated valve body is comprised of at least two parts, with a first part including said inlet port, said umbrella check valve, and those portions of the inner wall on an inlet-port side of a point of maximum width of the internal channel, and a second part including those portions of the interior wall on an outlet-port side of the point of maximum width and the outlet port.

3. The check valve assembly of claim 1, wherein the elongated valve body is comprised of at least two parts:
    a first part including said inlet port, said umbrella check valve, a first annular wall portion, and an inlet-side subportion of a second annular wall portion with a radial separation from the central longitudinal axis according to Equations (1) and (3); and
    a second part including an outlet-side subportion of the second annular wall portion with a radial separation from the central longitudinal axis according to Equations (2) and (3), a third annular wall portion with a radial separation from the central longitudinal axis according to Equations (2) and (3), and said outlet port.

4. The check valve assembly of claim 3, wherein said second part includes a cylindrical inner wall portion adjoining said outlet-side subportion of said second annular wall portion, said cylindrical inner wall portion receiving and engaging a cylindrical outer wall portion of said first part upon assembly of the check valve assembly.

5. The check valve assembly of claim 4, wherein said first part includes a land adjoining the cylindrical outer wall portion of said first part, and second part includes an opposing land adjoining the cylindrical inner wall portion of said second part, said cylindrical inner wall portion receiving and engaging the cylindrical outer wall portion of the said first part upon assembly of the check valve assembly.

6. The check valve assembly of claim 4, wherein said cylindrical outer wall portion of said first part and said cylindrical inner wall portion of said second part are joined by ultrasonic welding, solvent welding, or an adhesive.

7. A check valve assembly comprising:
an elongated valve body having an inlet port, an outlet port, and an internal channel communicating between said inlet port and said outlet port, each disposed about and generally aligned with a central longitudinal axis of the valve body;
said inlet port including an umbrella check valve disposed at an entrance to said internal channel and configured to obstruct reverse flow from said internal channel into said inlet port;
a distance along said central longitudinal axis from the entrance to said internal channel toward the outlet port being denoted as x, and a radial separation of an interior wall of the internal channel from the central longitudinal axis being denoted as r, with r varying with x according to:

$$r'=12.25+\operatorname{SQRT}(7.5625-(x-2.75)^2) \text{ for } 0<x<2.75 \text{ and } r'>12.25; \quad \text{Equation (4)}$$

$$r'=0.00003{*}x^5-0.002{*}x^4+0.0506{*}x^3-0.5724{*}x^2+2.1563{*}x+12.456 \text{ for } 2.75<x<18.1; \text{ and} \quad \text{Equation (5)}$$

$$r(x)=r'(x)\pm 2.0, \text{ where } \pm \text{ denotes a tolerance}, \quad \text{Equation (6)}$$

with the separation r defining an essentially continuously curved interior surface.

8. The check valve assembly of claim 7, wherein the elongated valve body is comprised of at least two parts, with a first part including said inlet port, said umbrella check valve, and those portions of the inner wall on the inlet-port side of a point of maximum width of the internal channel, and a second part including those portions of the inner wall on an outlet-port side of the point of maximum width and the outlet port.

9. The check valve assembly of claim 7, wherein the elongated valve body is comprised of at least two parts:
a first part including said inlet port, said umbrella check valve, a first annular wall portion, and an inlet-side subportion of a second annular wall portion with a radial separation from the central longitudinal axis according to Equations (4) and (6); and
a second part including an outlet-side subportion of the second annular wall portion with a radial separation from the central longitudinal axis according to Equations (5) and (6), a third annular wall portion with a radial separation from the central longitudinal axis according to Equations (5) and (6), and said outlet port.

10. The check valve assembly of claim 9, wherein said second part includes a cylindrical inner wall portion adjoining said outlet-side subportion of said second annular wall portion, said cylindrical inner wall portion receiving and engaging a cylindrical outer wall portion of said first part upon assembly of the check valve assembly.

11. The check valve assembly of claim 10, wherein said first part includes a land adjoining the cylindrical outer wall portion of said first part, and second part includes an opposing land adjoining the cylindrical inner wall portion of said second part, said cylindrical inner wall portion receiving and engaging the cylindrical outer wall portion of the said first part upon assembly of the check valve assembly.

12. The check valve assembly of claim 10, wherein said cylindrical outer wall portion of said first part and said cylindrical inner wall portion of said second part are joined by ultrasonic welding, solvent welding, or an adhesive.

* * * * *